US012702395B2

(12) United States Patent
Tritto et al.

(10) Patent No.: US 12,702,395 B2
(45) Date of Patent: Aug. 11, 2026

(54) APPLICATOR OF A SPONGEOUS COLLAGEN MEMBRANE AND KIT COMPRISING SUCH APPLICATOR AND MEMBRANE

(71) Applicant: GEISTLICH PHARMA AG, Wolhusen (CH)

(72) Inventors: Michael Tritto, North Potomac, MD (US); Niklaus Stiefel, Lucerne (CH); Raphael Kaufmann, Ruswil (CH); Mark Spilker, Kilchberg (CH)

(73) Assignee: GEISTLICH PHARMA AG, Wolhusen (CH)

( * ) Notice: Subject to any disclaimer, the term of this patent is extended or adjusted under 35 U.S.C. 154(b) by 378 days.

(21) Appl. No.: 18/248,427

(22) PCT Filed: Oct. 14, 2021

(86) PCT No.: PCT/EP2021/078484
§ 371 (c)(1),
(2) Date: Apr. 10, 2023

(87) PCT Pub. No.: WO2022/079186
PCT Pub. Date: Apr. 21, 2022

(65) Prior Publication Data

US 2023/0389911 A1 Dec. 7, 2023

(30) Foreign Application Priority Data

Oct. 15, 2020 (EP) .................................... 20202063

(51) Int. Cl.

| | |
|---|---|
| ***A61B 17/00*** | (2006.01) |
| ***A61L 27/24*** | (2006.01) |
| ***A61L 27/56*** | (2006.01) |

(52) U.S. Cl.
CPC .... *A61B 17/0057* (2013.01); *A61B 17/00234* (2013.01); *A61L 27/24* (2013.01);
(Continued)

(58) Field of Classification Search
CPC ...... A61B 17/0057; A61B 2017/00349; A61B 2017/00623; A61F 2/0063; A61F 2/0095;
(Continued)

(56) References Cited

U.S. PATENT DOCUMENTS 5,310,407 A * 5/1994 Casale ............ A61B 17/12022
604/59
6,713,085 B2 3/2004 Geistlich et al.
(Continued)

FOREIGN PATENT DOCUMENTS

CH 396311 A 7/1965
EP 2436342 B1 5/2013
(Continued)

OTHER PUBLICATIONS

English Machine Translation of Description of WO2020045933 A1 (Jung et al.) from Patentscope website <https://patentscope.wipo.int/search/en/detail.jsf?docId=WO2020045933&_cid=P22-MAK7SP-77494-1>, accessed May 11, 2025. (Year: 2025).*
(Continued)

*Primary Examiner* — Diane D Yabut
(74) *Attorney, Agent, or Firm* — Rothwell, Figg, Ernst & Manbeck, P.C.

(57) ABSTRACT

The invention provides an applicator of a spongeous collagen membrane and a kit comprising such applicator and such membrane. The applicator comprises an applicator body having a guide extending in a direction from the proximal end to the distal end of the applicator body and a sliding element slidably comprising a shaft portion movable along the guide. The sliding element is provided at its distal
(Continued)

end with a contact portion for contacting the spongeous collagen membrane, and the contact portion of the sliding element comprises mechanical fixation means configured to releasably hold the spongeous collagen membrane without substantially generating forces acting in the distal direction on the spongeous collagen membrane over its area extension. The distal end of the applicator body comprises a release surface configured to apply a release force to the spongeous collagen membrane releasing it from the mechanical fixation means for application to the wound site. In this way, it is possible to prevent compression of the fragile membrane and maintain its properties during handling and placement onto the wound site.

25 Claims, 2 Drawing Sheets

(52) U.S. Cl.
CPC ..... *A61L 27/56* (2013.01); *A61B 2017/00349* (2013.01); *A61B 2017/00623* (2013.01)

(58) Field of Classification Search
CPC .............. A61F 2002/0072; A61F 13/26; A61F 13/266; A61F 13/00085; A61F 15/005; A45D 2200/10; A45D 2200/1009; A45D 2200/1018; A45D 2200/1027
See application file for complete search history.

(56) References Cited

U.S. PATENT DOCUMENTS

2003/0236573 A1 12/2003 Evans et al.
2004/0146433 A1* 7/2004 Massaro ................ B01L 3/022 422/63
2005/0095275 A1 5/2005 Zhu et al.
2006/0051155 A1* 3/2006 Delage ................. A45D 40/267 401/122
2008/0039805 A1 2/2008 Frederickson et al.
2009/0012629 A1* 1/2009 Yao .................... A61F 2/30756 623/23.72
2011/0270394 A1* 11/2011 Herford ................. A61P 17/00 623/15.12
2012/0259349 A1* 10/2012 Brahm .................. A61B 17/00 606/151
2013/0142840 A1* 6/2013 Giraud-Guille ......... A61L 27/24 514/17.2
2014/0243747 A1 8/2014 Tokumoto et al.
2016/0022861 A1* 1/2016 Macphee ................ A61L 15/32 604/15
2016/0101272 A1 4/2016 McAllister
2016/0271380 A1* 9/2016 Poon ................ A61M 37/0015
2017/0281266 A1* 10/2017 Slatkine ............. A61B 18/1477
2019/0290262 A1* 9/2019 Fischer ............. A61B 17/0057
2020/0061246 A1 2/2020 Marmorstein et al.

FOREIGN PATENT DOCUMENTS

EP 3055000 B1 12/2016
WO WO-2020045933 A1 * 3/2020 ........ A61M 37/0015

OTHER PUBLICATIONS

International Search Report and Written Opinion issued in PCT/EP2021/078484 mailed Jan. 4, 2022, 14 pgs.

* cited by examiner

APPLICATOR OF A SPONGEOUS COLLAGEN MEMBRANE AND KIT COMPRISING SUCH APPLICATOR AND MEMBRANE

CROSS REFERENCE TO RELATED APPLICATIONS

This application is a 35 U.S.C. 371 National Phase Entry Application from PCT/EP2021/078484 filed Oct. 14, 2021, which claims priority to and the benefit of European Patent Application No. 20202063.2, filed on Oct. 15, 2020, the disclosures of which are incorporated herein by reference in their entirety.

TECHNICAL FIELD

The present invention relates to surgical instruments, specifically to applicators of materials such as a collagen membrane, a collagen sponge or a combination thereof, for use as a medical device for treating subjects suffering from various soft tissue defects or wounds, such as notably chronic ulcers, in particular chronic skin ulcers. The subject-matter also relates to a kit comprising the mentioned applicator and a spongeous collagen membrane, which is useful notably for the treatment of chronic ulcers.

STATE OF THE ART AND TECHNICAL PROBLEM

A recently developed treatment for chronic ulcers, in particular chronic skin ulcers, consists in cleaning and debriding the wound until viable tissue is exposed, and applying onto the wound bed an aseptical implant in form of a spongeous collagen material which consists of a single or multilayer sheet of collagen membrane material. That implant may comprise a sponge-like matrix layer of collagen which increases the liquid uptake capacity of the implant and promotes tissue ingrowth. The implant is placed dry, then hydrated with blood or isotonic solution and finally fixed with appropriate wound dressing. Such single or multi-layer spongeous collagen membranes have also been known for the treatment of wounds in the oral mucosa (see U.S. Pat. No. 6,713,085 B2) or the treatment of soft tissue defects (see EP 3 055 000 B1).

With the increase of potential fields of application of the above-mentioned spongeous collagen membrane, also the challenges due to the specific implantation site physiology have increased. Currently, the surgeon holds the implant by means of forceps or tweezers or directly with his glove-protected fingers during the transfer from the packaging tray, during possible cutting (to adapt the implant to the wound site) and during placement into the wound site.

In particular, such handling is necessary to allow the surgeon to adapt the implant to the specific shape of the wound, for example irregular, strongly curved wound sites such as those occurring in-between the toes, commonly encountered in diabetes-induced chronic skin ulcers DFU, or in the buccal region.

However, the Applicant has identified several technical problems of this type of handling by means of forceps, tweezers or the surgeon's fingers. On the operative side, there is the contamination of the surgeon's gloves with exudate from the wound which, among others, increases the risk of contamination of tissue adjacent to the wound site. Such risk may also be present when employing forceps or tweezers, as also these may unwillingly contact the wound site and then potentially transfer pathogens. In this context, mechanical irritation of the wound bed can occur if the surgeon unwillingly contacts the wound bed with the lower half of the forceps, tweezers or with his fingers. In addition, the mentioned handling methods always require a separate set of sterile, auxiliary forceps or tweezers which were not used beforehand for the decontamination and debridement of the surgical site.

On the structural side, the Applicant has realized that the described conventional handling methods, which are known from the placement of haemostatic patches, for example, are unsuited to the placement of spongeous collagen implants as they may actually damage or otherwise impair the implant or render it less effective. The conventional methods of handling of the implant when removing it from the package and placing it inevitably lead to a certain degree of local compression of the implant by the fingers, forceps or tweezers, which causes a reduction in liquid uptake capacity by a reduction of the porosity in the spongeous membrane. Both effects lead to reduced cell migration and thus negatively affect the healing process. There is further the danger of a mechanical destruction of the spongy part of the implant during removal of the forceps when hydrating the implant due to the decrease in structural rigidity of the spongy part when wet, especially for the spongeous collagen membrane disclosed in U.S. Pat. No. 6,713,085 B2, where, due to the absence of any artificial (non-natural) crosslinking, the spongy part is mechanically very fragile as soon as it gets wet (which may happen upon placement in the vicinity of chronic ulcers or oral surgical sites).

Further, while applicators of various medical material are known, such as applicators in the form of syringes used for example to place granules (see Bio-Oss Pen®, available from Geistlich AG, and EP-2'436'342), pastes or self-setting liquids (e.g. fibrin glue), or guiding templates for the placement of load bearing implants (e.g. dental implants, hip implants etc.), or arthroscopic tubing to place e.g. stents, none of these applicators is designed and configured to adequately address the specific properties and mechanical characteristics of fragile spongeous collagen membranes.

SUMMARY OF THE INVENTION

In order to overcome the above-described problems, the invention provides an applicator for a spongeous collagen membrane which holds the spongeous collagen membrane in a manner so that the properties of the spongeous collagen membrane remain unaltered while at the same time ensuring high sterility and ease of use regarding cutting and placement of the wound treatment. An applicator of this type is defined in claim 1. Further, the invention provides a kit comprising the applicator and the spongeous collagen membrane as defined in claim 8. Optional and/or preferred embodiments are defined in the respective dependent claims.

According to the invention, an applicator of a spongeous collagen membrane comprises: an applicator body having a proximal end and a distal end and having or defining a guide extending in a direction from the proximal end to the distal end, a sliding element slidable along the guide of the applicator body and having a proximal end for handling by the user, the sliding element being provided at its distal end with a contact portion for contacting the spongeous collagen membrane, the contact portion being configured to extend to or past the distal end of the applicator body when sliding the sliding element. The contact portion of the sliding element comprises mechanical fixation means configured to releasably hold the spongeous collagen membrane without substantially generating forces acting in the distal direction on the spongeous collagen membrane over its area extension, and the distal end of the applicator body comprises a release surface configured to apply a release force to the spongeous collagen membrane releasing it from the mechanical fixation means for application to the wound site.

In use, the operator or user (usually a surgeon), applies the applicator to the spongeous collagen membrane so as to engage it with the mechanical fixation means, which thus hold the spongeous collagen membrane. Since the mechanical fixation means do not substantially generate forces acting in the distal direction on the membrane, the membrane is not compressed in a thickness direction thereof. Gripping the proximal end of the sliding element, he then slides the sliding element with respect to the applicator body to engage the release surface with the spongeous collagen membrane and transmit the release force which disengages the spongeous collagen membrane from the mechanical fixation means.

A suitable "spongeous collagen membrane" is for instance a single- or multilayer-membrane or matrix of collagen material which comprises a spongeous part combined with a membrane, or a sponge of collagen material.

The term "collagen material" refers to the combination of 60-100% (w/w) collagen and 0-40% elastin that is usually present in tissues of natural origin.

The term "without substantially generating forces acting in the distal direction" is to be understood in the sense that the mechanical fixation means holding the spongeous collagen membrane without generating significant force components in the thickness direction of the spongeous collagen membrane over its area extension, i.e. over the extension of its distal and/or proximal surfaces, which are capable of leading to a partial or total compression or crushing of the spongeous collagen membrane. In other words, the force per unit area generated by the mechanical fixation means must be smaller than the mechanical breakdown pressure of the spongeous collagen membrane in as much of the membrane surface as possible. Such force components may occur, for example, when the spongeous collagen membrane is held by forceps, tweezers or the fingers. The force-exercising contact areas of forceps, tweezers and fingers are flat and such forceps, tweezers and fingers, even when handled gently, still provide forces which may become too large for the spongeous collagen membrane. In fact, since a spongeous collagen membrane can be very fragile, having for instance an initial modulus of elasticity of approximately 200 kPa in the dry state and approximately 2 kPa in the hydrated state (as exhibited by the spongeous collagen membrane disclosed in U.S. Pat. No. 6,713,085), already the normal holding forces by the fingers, forceps or tweezers acting on the contact areas may lead to irreversible compression of in particular the hydrated membrane across significant portions of its area extension (surface area), with the negative consequences outlined above.

The term "release force" is to be understood not as a force acting as compressive force on the membrane across its area extension but as a force sufficient to release the spongeous collagen membrane from the action of the mechanical fixation means, i.e. to overcome its fixation or holding force. For example, the release force may be such as to be distributed across the area extension of the spongeous collagen membrane so that the force per surface area applied remains low enough not to cause substantial compression of the spongeous collagen membrane across its area extension. In another example, the release force may act only on a peripheral portion of the spongeous collagen membrane, thereby avoiding any force input on the majority of its area extension and thus avoiding a compression of the spongeous collagen membrane.

In certain embodiments of the invention, the applicator body is hollow and defines an internal channel serving as the guide, and the sliding element is a plunger slidable within the channel. The internal channel extends from the proximal end to the distal end of the applicator body. For example, the applicator body may be tube shaped and have a proximal opening at its proximal end and at least a distal opening at its distal end.

In certain embodiments of the invention, the mechanical fixation means comprise one or more needles configured for penetrating into and holding the spongeous collagen membrane. Due to their configuration for penetration, i.e. by having a sharp pointed end, these needles have a very small curvature radius, usually from 50 to 200 μm (approx. 65 μm for needles made from steel, approx. 200 μm for 3D printed plastic needles) and thus a very small front surface at their tip (i.e. the surface facing the membrane) which is a negligibly small fraction of the area extension of the membrane, and thus, when penetrating the spongeous collagen membrane, the needles experience very little resistance and generate only negligible, i.e. substantially no forces on the spongeous collagen membrane across its area extension in the distal direction, the thickness direction of the spongeous collagen membrane. Thus, while the needle generates a sufficient force for penetrating the membrane, this force is limited to a very small area compared the area extension of the spongeous collagen membrane and no compression of the fragile spongeous collagen membrane occurs (except of course in the negligible area occupied by the penetration holes). After penetrating into the spongeous collagen membrane, the flanks of the needles are in contact with the collagen material of the spongeous collagen membrane and generate just sufficient frictional force to allow the needles to hold the spongeous collagen membrane against the action of gravity. This holding force of the needles is limited because it is only determined by the frictional resistance between the flanks of the needles and the spongeous collagen membrane material, which depends on the number of needles and the resulting force caused by the needles penetrating into the membrane. The fact that the holding force is provided by the rather weak frictional forces between the needles and the spongeous collagen membrane has the advantageous consequence that very little release force is needed to overcome the weak frictional forces to release the spongeous collagen membrane from the needles (mechanical fixation means) when the spongeous collagen membrane is released toward the wound site. This avoids large forces being applied in the thickness direction of the spongeous collagen membrane. All this contributes to the advantage that the spongeous collagen membrane retains its physical properties throughout the handling process by means of the applicator of the invention and thus can provide the desired effects of liquid uptake and tissue ingrowth.

The needles are preferably solid, i.e. non-hollow needles which aid in penetration and avoid collagen material being trapped in the needle lumen. The needle material is preferably pharmaceutical steel, but it is also possible to injection-mould the contact portion and the one or more needles, e.g. by single or two-component injection moulding or to use 3D printing.

The number of needles is preferably two or more, particularly preferably four or more and particularly preferably six or more. By using a plurality of needles, the holding force is increased without acting on a single location of the spongeous collagen membrane. Preferably, the needles are substantially evenly distributed on the contact portion of the sliding element (plunger). In this way, an optimal distribution of the total holding force provided by the needles across the area extension of the spongeous collagen membrane is achieved, i.e. the force acting on a unit surface area of the spongeous collagen membrane is minimized both during insertion of the needles and during their removal for delivery to the wound site. This helps in keeping the forces acting in the distal direction on the spongeous collagen membrane over its area extension low enough so as to cause no substantial compression of the spongeous collagen membrane. In this way, the spongeous collagen membrane can retain its properties during the entire application process of the spongeous collagen membrane.

In a preferred embodiment, the distal end of the applicator body comprises a plurality of distal openings, each aligned with the plurality of needles. The release surface hence is defined by the distal end of the applicator body not occupied by the distal openings. The distal openings may be sized with sufficiently small clearance to securely let pass the needles. Thus, the total area occupied by the distal openings can be made small with respect to the area of the release surface, e.g. the total area occupied by the distal openings being less than 25%, less than 20%, less than 15%, less than 10%, less than 5%, or less than 3% of the area of the release surface. Since this release surface, i.e. the solid area of the distal end, is more extended or larger than the surface occupied by the distal openings, the limited, small force required to release the spongeous collagen membrane from the needles (mechanical fixation means) is distributed across an area of contact as extended or large as possible, and very little pressure (force per unit area) is applied to the spongeous collagen membrane to release it. Thus, the spongeous collagen membrane is subjected to no substantial compression and maintains its properties unaltered by the handling with the applicator of the invention.

Preferably, the applicator body comprises a removable distal end cap which comprises the plurality of distal openings. In this manner, it is possible to use disposable caps for the applicator that can be changed after each use to increase sterility of the applicator.

The applicator body and its portions, as well as the sliding element (plunger) and its portions can be injection moulded from medical grade plastics and surface-treated and sterilized as is well known in the art. Further, they can also be formed by 3D printing from medical grade resins. For example, the material of the applicator body may be PA Duraform white (USP Class IV/FDA) and be printed by selective laser sintering (SLS), while the material of the sliding element (plunger) may be Somos® WaterShed XC 11122 and by printed by Stereolithography (SLA). Both materials are biocompatible for short term (<24 hours) contact.

In a preferred embodiment, the applicator comprises a biasing means biasing the sliding element and the applicator body with respect to each other along the direction of the internal channel. For example, such biasing means may be a spring. When the user wishes to slide the plunger with respect to the applicator body, he has to overcome the force of this biasing means. The parameters of the biasing means are conveniently chosen in such way as to set this force in a range which can be overcome by the user's fingers, for example by choosing an appropriate spring constant and length. In this way, it is possible to define a rest condition between the sliding element and the applicator body, in which the biasing means applies a first force (such as zero or only a small biasing force), and an actuated condition in which the biasing means applies a second force larger than the first force.

For example, the rest condition can correspond to a relative positioning in which the contact portion of the sliding element is withdrawn proximally past the distal end of the applicator body and the proximal portion of the sliding element, e.g. configured as a button waiting to be engaged by the user, protrudes from or beyond the proximal end of the applicator body. When the user engages and actuates the proximal portion of the sliding element against the biasing force of the biasing means, he brings the applicator into the actuated position in which the contact portion of the sliding element is passed up to or past the distal end of the applicator body. Instead of a button, it is of course possible to provide different mechanisms for actuating the sliding element, such as by sliders, rotary (including threaded) mechanisms and so on.

In another embodiment, the applicator body may be bent so as to better conform to the geometry of wound sites, e.g. in oral settings. Correspondingly, also the sliding element is bent any may be formed from a flexible material.

In another aspect, the invention provides a kit comprising an applicator and a spongeous collagen membrane (M), wherein the spongeous collagen membrane comprises a sheet of collagen material in dry state wherein the sheet of collagen material comprises a spongeous matrix layer of collagen material having an open sponge-like texture. In some aspects, the sheet of collagen material is a multi-layer sheet of collagen material further comprising a barrier layer of collagen material having a smooth face and a rough face opposite said smooth face and a spongeous matrix layer of collagen material connected to said fibrous face, said spongeous matrix layer of collagen material having an open sponge-like texture. In some aspects, a kit according to the present disclosure includes a spongeous collagen membrane releasably held by the applicator. In that kit, preferably, the contact portion (22*b*, 32*b*) of the sliding element (22, 32) of the applicator (20, 30) contacts the smooth surface of the barrier layer, and the spongeous matrix layer of collagen material is connected to said rough fibrous face, such that the rough fibrous face of said barrier layer of collagen material to which is connected said spongeous matrix layer of collagen material having an open sponge-like texture, faces distally the wound or implantation site.

The open sponge-like structure of the matrix layer gives the spongeous collagen membrane a high liquid uptake capacity and may provide a scaffold for increased cell mobility and ingrowth. Further, since the spongeous collagen membrane is releasably held by the applicator without substantially generating forces acting in the distal direction on the spongeous collagen membrane over its area extension and the release force is correspondingly limited, the spongeous collagen membrane is not substantially compressed during use of the kit (taking up the spongeous collagen membrane with the applicator, holding it, placing it and releasing it), maintaining its mentioned advantageous properties intact. Moreover, the kit provides the desired effects of distancing the user's hands from the wound site and avoiding any contact between the wound site and both of the user's hands and the applicator. This drastically lowers the risk of contamination of the user's hands, as well as any mechanical irritation of the wound bed. Also, since the applicator avoids contact with the wound site, it is not necessary to provide a separate set of sterile forceps or tweezers.

Preferably, the sheet of collagen material is a multi-layer sheet of collagen material, further comprising a barrier layer of collagen material having a smooth face and a rough fibrous face opposite said smooth face, wherein the spongeous matrix layer of collagen material is connected to said rough fibrous face, such that the rough fibrous face of said barrier layer of collagen material to which is connected said spongeous matrix layer of collagen material having an open sponge-like texture, faces distally.

Providing an additional barrier layer further increases the mechanical protection of the spongeous matrix layer and thus of its advantageous properties as well as increasing sterility of the wound site. Moreover, the barrier layer inhibits direct cell migration through the collagen material and thus provides protection to newly generated tissue from outside influences.

Preferably, an area of overlap between the spongeous collagen membrane and the applicator is smaller than the area extension of the spongeous collagen membrane. This allows cutting of the membrane to the desired size and shape while holding it with the applicator, e.g. with a scalpel, shears, scissors or the like, in order to form an implant.

In certain embodiments, the kit includes a blister or a peel pouch for storing the spongeous collagen membrane, and instructions for use of the applicator and the spongeous collagen membrane. Preferably, the kit may also comprise a pouch for receiving the blister or peel pouch, the applicator and the instructions for use.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE FIGURES

The accompanying drawings, which are incorporated herein and form part of the specification, illustrate various exemplary and non-limiting aspects of the subject matter this disclosure. In the drawings, like reference numbers indicate identical or functionally similar elements.

DETAILED DESCRIPTION

While aspects of the subject matter of the present disclosure may be embodied in a variety of forms, the following description and accompanying figures are merely intended to disclose some of these forms as specific examples of the subject matter encompassed by the present disclosure. Accordingly, the subject matter of this disclosure is not intended to be limited to the forms or embodiments so described and illustrated.

Figures 1A, 1B, 1C, 1D, 2A, 2B, 2C, 2D:
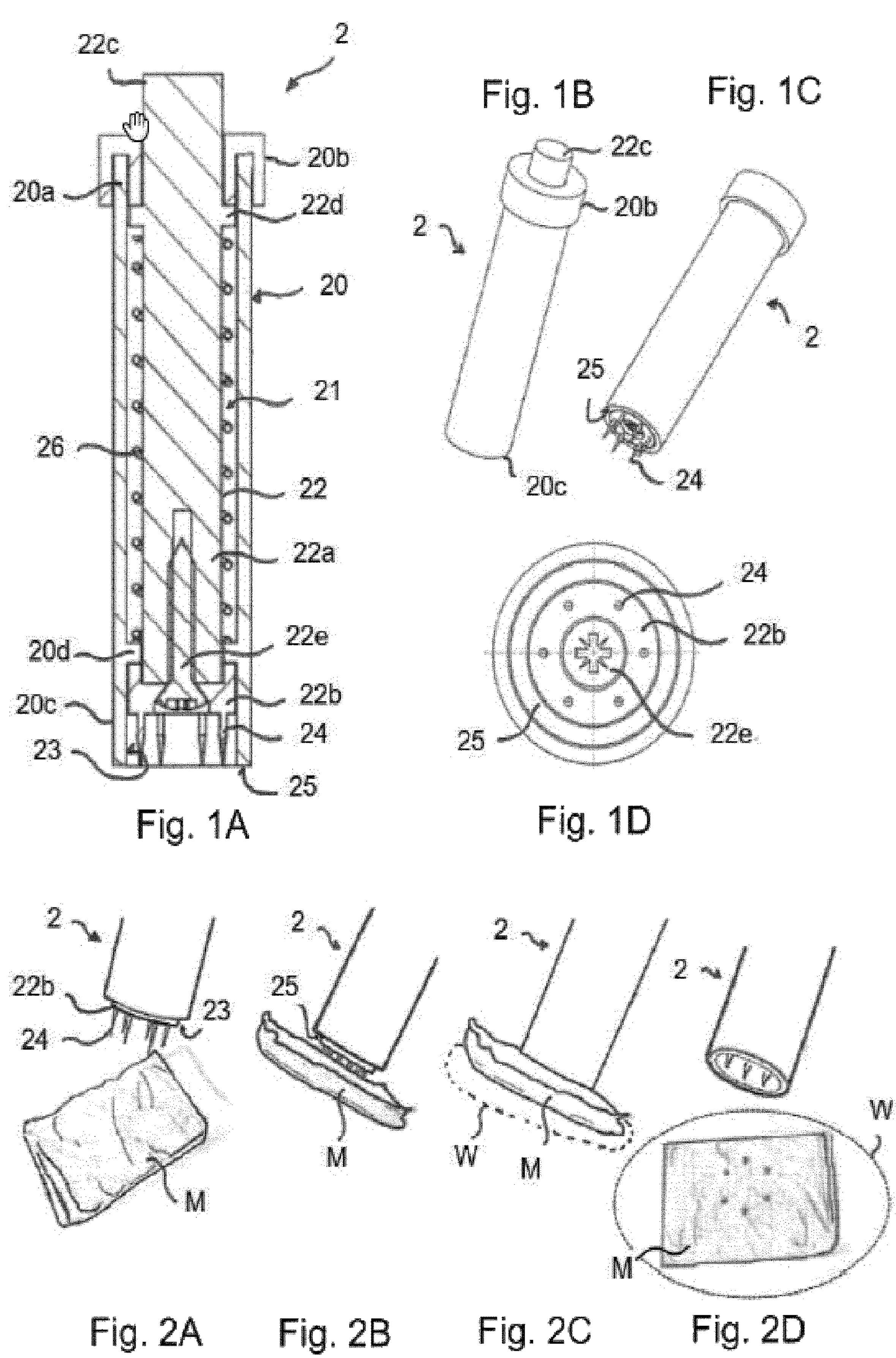
FIGS. 1A-1D show a first embodiment of the applicator of the present invention, with FIG. 1A showing a longitudinal sectional view, FIGS. 1B and 1C showing perspective views and FIG. 1D showing a plan view of the distal end of the applicator (2)
FIGS. 2A-2D show a kit comprising the applicator (2) of FIGS. 1A-1D during successive steps of its use, individually shown in FIGS. 2A-2D.

FIGS. 1A-1D show a first embodiment of the applicator 2 of the present invention. FIG. 1A is a longitudinal sectional view of the applicator, FIGS. 1B and 1C are perspective views from top and bottom, respectively, and FIG. 1D is a plan view of the distal end of the applicator. The applicator 2 comprises an applicator body 20 having a proximal end 20*a* and a distal end 20*c*. The body 20 of applicator 2 in this embodiment has a cylindrical shape and is provided with a distal opening 23 at its distal end 20*c*. However, the shape of the applicator body 20 may be varied and is not intended to be limited, e.g. a rectangular tube-shape may be used. The distal opening 23 has a distally facing release surface 25, surrounding the opening 23. The applicator body 20 defines an internal guide channel 21 along its longitudinal axis L in which a sliding element, e.g. plunger 22 is slidably movable back and forth in an axial direction, i.e. a proximal to distal direction. The sliding element, e.g., plunger 22 has a shaft portion 22*a* having a proximal end, a distal contact portion 22*b* for contacting the spongeous collagen membrane M and a proximal portion 22*c* for handling/engagement by the user. In one embodiment, the proximal portion 20*a* of the applicator body 20 is covered by a removable cap 20*b* which engages the wall of the proximal portion 20*a* (e.g. by a screw connection) and is provided with a central opening through which the proximal portion 22*c* can pass. Thus, as shown in FIGS. 1B and 1C, in this embodiment the proximal portion 22*c* of the sliding element, e.g., plunger 22 can be configured as a push-button (e.g. for the thumb), and the cap 20*b* can serve as a gripping portion (for example for the index and middle fingers). However, the proximal portion 20*a* (FIG. 1A) can also be provided with a proximal opening without cap or be provided with a cap as described, but integral rather than removable, e.g. fixed to the proximal end 20*a* by gluing or welding.

In this embodiment, the contact portion 22*b* of the plunger is cylindrical and is provided at its distal surface with mechanical fixation means in form of penetrating needles 24 which extend distally from the contact portion 22*b*. As a non-limiting example, FIG. 1D shows six penetrating needles spaced equidistantly along a circle close to the periphery of the contact portion 22*b*. The needles are penetrating in the sense that they feature a pointed tip with a curvature radius that is sufficiently small so that upon contact with the spongeous collagen membrane M the needles pierce and penetrate into the spongeous collagen membrane without substantial resistance and, thus, do not generate substantial forces in the spongeous collagen membrane's thickness direction across the area extension of the spongeous collagen membrane. Of course, more or fewer needles can be provided, and they may be distributed in a manner across the distal surface of the contact portion 22*b*, e.g., evenly or regularly, so as not to generate compression of the spongeous collagen membrane. On the one hand, for very small spongeous collagen membranes and, thus, applicators even one needle may be sufficient. On the other hand, two or more needles provide larger and better distributed holding forces which prevent the spongeous collagen membrane from accidentally falling off, e.g. during handling and placement, i.e. before its intended release. Without limitation, a suitable exemplary number of needles per unit area of the distal surface of the contact portion may be between 0.5 and 20 needles per $cm^2$, preferably between 1.5 and 15 needles per $cm^2$.

The spongeous collagen membrane M is preferably a multi-layer sheet of collagen material, with a barrier layer of collagen material having a smooth face and a rough fibrous face opposite said smooth face, and a spongeous matrix layer of collagen material having an open sponge-like texture which is connected to said rough fibrous face, such that the rough fibrous face of said barrier layer of collagen material faces distally.

A spring 26, e.g., a helical spring, as biasing member is arranged in the channel 21 and surrounds plunger shaft portion 22*a*. One end of the spring 26 engages a plunger collar 22*d*, which projects outwardly from the shaft portion 22*a* of the plunger near the proximal end 22*c* of the plunger, and a body collar 20*d* which projects inwardly from the walls of the applicator body into the channel 21 and is provided distally from the plunger collar 22*d*, in this embodiment close to the distal end 20*c* of the applicator body 20. In this manner, the spring 26 biases the plunger in a proximal direction so that the proximal portion 22*c* of the plunger protrudes out of the proximal end 20*a* and the cap 20*b* and is ready to be pushed or depressed by the user. At the same time, the contact portion 22*b* of the plunger is withdrawn into the applicator body and does not protrude beyond the distal opening 23 thereof. This position corresponds to rest condition of the applicator.

When the user (e.g., a surgeon) pushes or presses the button 22*c*, i.e. the proximal end of the plunger 22, he pushes the plunger 22 distally against the force of the spring 26 so that the contact portion 22*b* of the plunger protrudes into and through the distal opening 23 of the applicator body (see FIG. 1C).

The contact portion 22*b* of the plunger is, in this embodiment, configured as a plate which is fixed to the plunger shaft portion 22*a* by a screw 22*e* or similar fixation means (see FIG. 1D). Also, the contact portion 22*b* configured as a plate has a larger diameter than the shaft portion 22*a* and engages in a proximal direction with the plunger collar 20*d* when the applicator reaches the rest condition. Thus, the plunger 22 is prevented from further moving out of the applicator body 20, and the contact portion 22*b*, including the penetrating and, thus, sharp needles, is securely kept within the applicator body.

FIGS. 2A-2D show an example of the use of the inventive applicator and kit. In FIG. 2A, the spongeous collagen membrane M is provided in its opened packaging, such as a blister (not shown), ready to be taken up by the applicator 2 held by a user, e.g., a surgeon. The user has depressed the proximal end (push-button) 22*c* of the plunger 22 (as previously described with respect to FIG. 1C) and has thus distally advanced the contact portion 22*b* with its needles 24 into and through the distal opening 23. The needles 24 are thus exposed and can take up the membrane M. The user orients the applicator with the distal end, i.e. its exposed needles 24, towards the spongeous collagen membrane. If the spongeous collagen membrane M comprises a multilayer sheet of collagen material with a spongeous matrix layer connected to a barrier layer of collagen material, the user positions the spongeous collagen membrane with the barrier layer, especially its smooth face, facing the distal end of the applicator. Then, he very lightly presses the applicator onto the spongeous collagen membrane M, perpendicularly to its surface, so that the needles penetrate into the membrane. Care is to be taken that the needles 24 do not perforate, i.e. pass through the spongeous collagen membrane M as then the needles have to be retracted into the spongeous collagen membrane prior placement onto the wound site to not damage the wound site. Since the spring 26 acts to withdraw the contact portion 22*b* against the pressing action of the user, use of excessive force onto the spongeous collagen membrane is prevented.

When the needles 24 have penetrated the spongeous collagen membrane M, as shown in FIG. 2B, the applicator securely holds the spongeous collagen membrane M so that it can be placed onto the wound site W. Once the spongeous collagen membrane M is in position on the wound site W (which is only schematically indicated by a dashed line), as shown in FIG. 2C, the user releases the pressure on the proximal portion 22*c* (push-button) of the plunger so that the contact portion 22*b* and the needles 24, with the membrane attached (held) to it, move proximally towards the applicator body 20 until the spongeous collagen membrane engages the release surface 25. Since the force of the spring 26 continues to retract the contact portion 22*b* and the needles 24, but the release surface 25 has engaged the spongeous collagen membrane M, the spongeous collagen membrane M is pulled off the needles 24 and released so that it can remain in position on the wound site W, as shown in FIG. 2D. Since the needles 24 are individually held in the membrane by limited frictional forces, and since they are distributed across the contact portion 22*b*, the release force necessary is limited and distributed across the area extension of the membrane so that the release force applied by the release surface 25 at the periphery of the applicator, i.e. around the holding area of the spongeous collagen membrane M on the contact portion 22*b*, is small and no substantive compression of the spongeous collagen membrane occurs either at the center or in other regions of the spongeous collagen membrane in contact with the applicator. This is in particular important in case the spongeous collagen membrane starts to hydrate upon placing into the wound.

The first embodiment is suitable for all sizes of the spongeous collagen membrane, in particular for small sizes and irregular shapes. For example, the applicator body 20 may have a diameter of 8 mm and thus allow application of membranes having sizes down to 8 mm. Also, given that the membrane is held by the contact portion 22*b* and needles 24 which are part of the mechanism of the plunger 22 and are surrounded by the distal release surface 25 of the applicator body 20, it is possible to deliver and release membranes having irregular shapes and sizes; the spongeous collagen membrane M can in fact be cut to specified shapes and sizes while it is held by the applicator 20. The cylindrical shape of the applicator body is further advantageous as it allows to reposition the applicator easily and thus cut around all sides of the spongeous collagen membrane if needed.

Figures 3A, 3B, 3C:
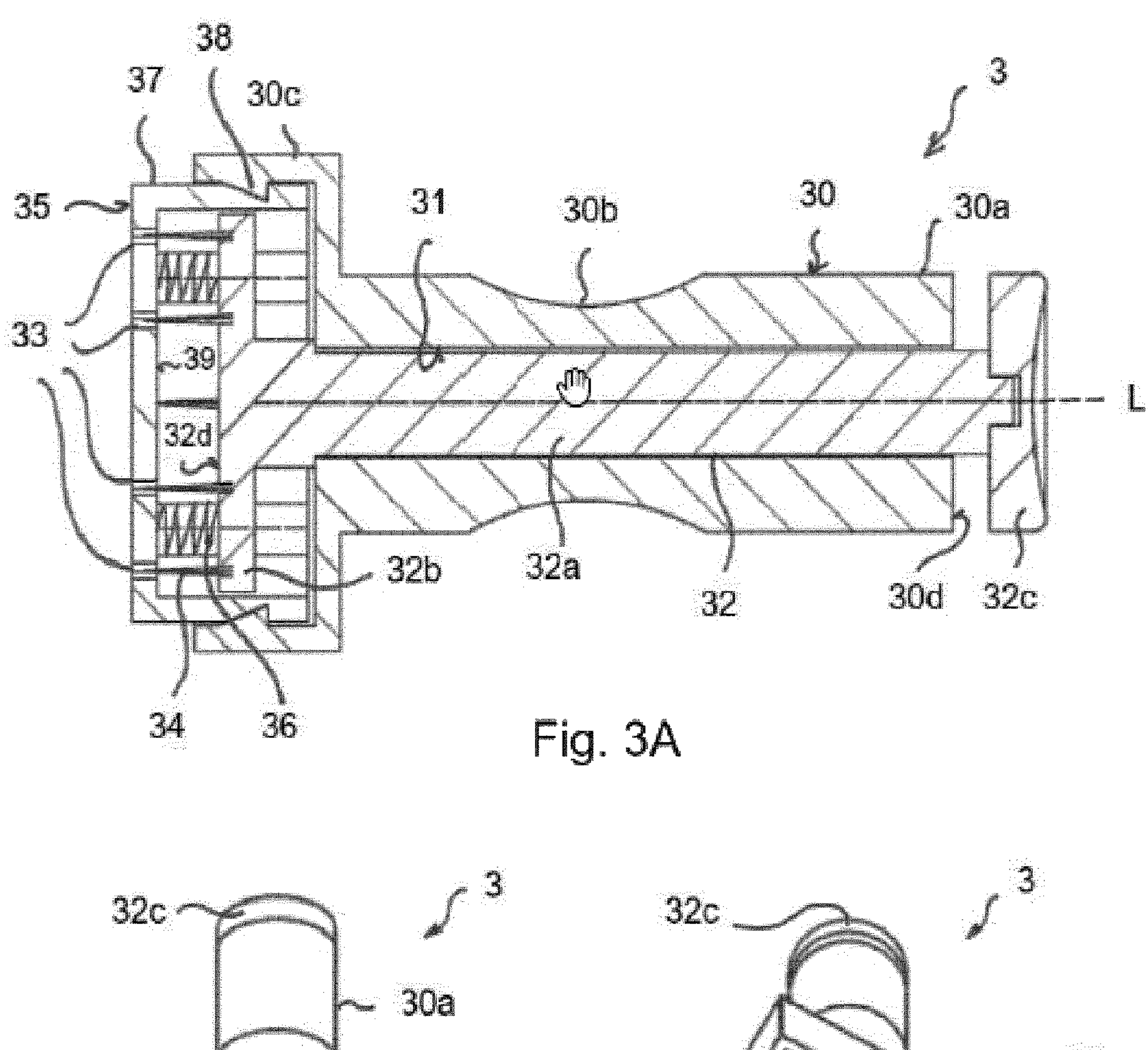
FIGS. 3A-3C show a second embodiment of the applicator (3) of the present invention, with FIG. 3A showing a longitudinal sectional view, and FIGS. 3B and 3C showing perspective views and seen from the distal end of the applicator (3).

A second embodiment of the inventive applicator and kit is shown in FIGS. 3A-3C. The structure of this embodiment is similar to the first embodiment and provides the same advantages. As shown in the longitudinal section of FIG. 3A, the applicator 3 comprises an applicator body 30 having a proximal end 30*a* and a distal end 30*c* and defining a channel 31 along its longitudinal axis L. The applicator body may have a recessed gripping portion 30*b* for better gripping of the applicator by the user. A plunger 32 is arranged within channel 31 in which it can slide back and forth in an axial direction, i.e. a proximal-distal direction. The plunger comprises a shaft portion 32*a*, a handle portion 32*c* and a contact portion 32*b* which has a larger transverse extension than the shaft portion 32*a* and serves for contacting the spongeous collagen membrane M. Correspondingly, the distal end 30*c* of the applicator body 30 is also transversely enlarged with respect to the proximal end 30*a* and the recessed portion 30*b*.

In this embodiment, in contrast to the first embodiment of FIGS. 1A to 1D, the applicator body has substantially a rectangular tube shape. The contact portion 32*b* of the plunger is also rectangular and is provided with mechanical fixation means in form of penetrating needles 34 which extend distally from the contact portion 32*b*. Here, thirty-four penetrating needles are arranged in a 5×7 matrix (no centre needle is provided) on the rectangular contact portion 32*b* (see FIGS. 3B and 3C). Of course, a different number and/or a different arrangement of needles, even just one needle for small membranes, can be provided with the aim not to generate compression of the spongeous collagen membrane. Without limitation, a suitable exemplary number of needles per unit area of the distal surface of the contact portion may be between 0.5 and 20 needles per $cm^2$, preferably between 1.5 and 15 needles per $cm^2$.

In contrast to the first embodiment, the applicator body 30 is provided with a distal cover 37 which covers its distal end 30*c* and has a distally facing release surface 35 provided with a plurality of through-holes 33 as distal openings in correspondence to the penetrating needles 34 of the plunger's contact surface 32*b*. The distal cover 37 is removably fixed to the distal portion 30*c* of the applicator body 30 via engagement with the detents 38 which engage in a known manner is corresponding recesses (not shown) on the distal cover 37. Further, between the proximally facing inner surface 39 of the distal cover 37 and the distal surface 32*e* of the contact portion 32*b*, four springs 36 are arranged so as to apply a biasing force pushing the plunger 32 proximally so that the needles 34 are withdrawn through the holes 33 into the applicator, i.e. into the space defined by the distal portion 30*c* of the applicator body and the distal cover 37. At the same time, the handle portion 32*c* is extended from the proximal end 30*a* of the applicator body ready to be depressed by the user. In this rest condition of the applicator 30, the needles 34 are safely stored inside the applicator so that the risk of injury or damage to the needles is minimized.

As shown in FIGS. 3B and 3C when the user depresses the handle portion 32*c* of the plunger in a distal direction, acting against the biasing force of springs 36, the plunger 32 moves distally and the penetrating needles 34 pass through the holes 33 until handle 32*c* abuts the proximal (top) surface 30*d* of the applicator body 30 or the distal surface 32*d* of the contact portion 32*b* abuts the inner surface 39 of the distal cover 37. The needles 34 now project distally from the opening and are ready for penetrating into the spongeous collagen membrane (not shown).

Once the spongeous collagen membrane M is taken up by the applicator 3 and positioned on the wound site, the user releases the pressure so that the force of springs 36 retracts the contact portion 32*b* and the needles 34 and the spongeous collagen membrane M comes into contact with the release surface 35. Since this release surface 35 occupies the majority of the contact surface with the spongeous collagen membrane M and only a small fraction of the contact surface with the spongeous collagen membrane M is occupied by the needles 34, which individually have a limited holding force and are distributed across the contact portion 32*b*, the release force exercised by the release surface 35 per unit area onto the spongeous collagen membrane M is very small and no substantial forces are applied in a spongeous collagen membrane thickness direction across the area extension of the spongeous collagen membrane, i.e. no compression of the fragile spongeous collagen membrane M can occur.

The invention claimed is:

1. An applicator (2, 3) of a spongeous collagen membrane (M) comprising:

an applicator body (20, 30) having a proximal end (20*a*, 30*a*) and a distal end (20*c*, 30*c*) and having a guide (21, 31) extending in a direction from the proximal end to the distal end, a sliding element (22, 32) comprising a shaft portion, extending inside the applicator body in a direction from the proximal end to the distal end and slidable along the guide of the applicator body and having a proximal end (22*a*, 32*a*) for handling by a user, the sliding element being provided at its distal end with a contact portion (22*b*, 32*b*) for contacting the spongeous collagen membrane (M), the contact portion being configured to extend to or past the distal end of the applicator body when sliding the sliding element, wherein the contact portion (22*b*, 32*b*) of the sliding element (22, 32) comprises mechanical fixation means (24, 34) configured to releasably hold the spongeous collagen membrane (M) without substantially generating forces acting in the distal direction on the spongeous collagen membrane over its area extension, and the distal end of the applicator body comprises a release surface (25, 35) configured to apply a release force to the spongeous collagen membrane (M) releasing it from the mechanical fixation means (24, 34) for application to a wound site (W), wherein the applicator body (20, 30) is hollow and defines an internal channel (21, 31) serving as the guide, and the sliding element is a plunger (22, 32) slidable within the channel, and wherein the plunger comprises a handle portion (32*c*) extended from the proximal end of the applicator body, wherein the handle portion (32*c*) is configured to act against biasing force of separate springs (36) such that depression of the handle portion causes the plunger to move distally to extend the mechanical fixation means (34) through the release surface (35).

2. The applicator (2, 3) according to claim 1, wherein the mechanical fixation means comprise one or more needles (24, 34) configured for penetrating into and holding the spongeous collagen membrane (M).

3. The applicator (3) according to claim 2, wherein the distal end of the applicator body (30) comprises a plurality of distal openings (33) and wherein each of the plurality of distal openings is aligned with one of the needles (34).

4. The applicator (2, 3) according to claim 3, wherein the applicator body (30) comprises a removable distal end cap (37) which comprises the plurality of distal openings (33).

5. The applicator (2, 3) according to claim 2, wherein the needles (34) have a curvature radius of 50 to 200 μm.

6. The applicator (2, 3) according to claim 1, further comprising a biasing means (26, 36) biasing the sliding element (22, 32) and the applicator body (20, 30) with respect to each other along the direction of the guide (21, 31).

7. The applicator (2, 3) according to claim 6, wherein the biasing means (26, 36) biases the sliding element (22, 32) and the applicator body (20, 30) in a direction in which the contact portion (22*b*, 32*b*) of the sliding element is withdrawn proximally past the distal end of the applicator body.

8. The applicator (2, 3) according to claim 6, wherein the biasing means comprises one or more springs.

9. The applicator (2, 3) according to claim 1, wherein the contact portion (22*b*, 32*b*) is a plate.

10. The applicator (2, 3) according to claim 9, wherein the shaft portion has a cylindrical shape, and the plate has a diameter larger than a diameter of the shaft.

11. A kit comprising the applicator (2, 3) of claim 10 and a spongeous collagen membrane (M), wherein the spongeous collagen membrane comprises a sheet of collagen material in dry state, wherein the sheet of collagen material comprises a spongeous matrix layer of collagen material having an open sponge-like texture.

12. The kit of claim 11, wherein the sheet of collagen material is a multi-layer sheet of collagen material further comprising a barrier layer of collagen material having a smooth face and a rough fibrous face opposite said smooth face and a spongeous matrix layer of collagen material connected to said rough fibrous face, said spongeous matrix layer of collagen material having an open sponge-like texture.

13. The kit of claim 12, wherein the contact portion (22*b*, 32*b*) of the sliding element (22, 32) of the applicator (20, 30) contacts the smooth face of the barrier layer, and wherein the spongeous matrix layer of collagen material is connected to said rough fibrous face, such that the rough fibrous face of said barrier layer of collagen material to which is connected said spongeous matrix layer of collagen material having an open sponge-like texture, faces distally.

14. The kit of claim 11, wherein the applicator is configured such that when the spongeous collagen membrane (M) is held by the applicator (2, 3), an area of overlap between the spongeous collagen membrane (M) and the applicator (2, 3) is smaller than the surface area of the spongeous collagen membrane (M).

15. The kit of claim 11, further including a blister or a peel pouch for storing the spongeous collagen membrane, and instructions for use of the applicator and the spongeous collagen membrane.

16. The kit of claim 11, wherein the spongeous collagen membrane is releasably held by the applicator.

17. A method of treating a chronic ulcer in a subject in need thereof comprising using the kit of claim 11 to release the spongeous collagen membrane (M) in the chronic ulcer of the subject.

18. A method of implanting a spongeous collagen membrane in a site of a subject comprising using the applicator of claim 1 to penetrate into the spongeous collagen membrane and to releasably hold the spongeous collagen membrane, then positioning the applicator holding the spongeous collagen membrane on the site, and releasing the spongeous collagen membrane from the applicator into the site.

19. The method of claim 18, wherein the penetrating step is performed by applying pressure to the proximal end of the applicator to extend the mechanical fixation means from the distal end of the applicator body and into the spongeous collagen membrane.

20. The method of claim 19, wherein the releasing step is performed by releasing the pressure applied to the proximal end of the applicator so as to retract the mechanical fixation means into the distal end of the applicator body.

21. The method of claim 20, wherein the releasing step includes engaging the spongeous collagen membrane with the release surface.

22. The applicator according to claim 1, wherein the springs (36) are arranged in parallel abutting an inner surface (39) of a distal cover (37).

23. An applicator (2, 3) of a spongeous collagen membrane (M) comprising:

an applicator body (20, 30) having a proximal end (20*a*, 30*a*) and a distal end (20*c*, 30*c*) and having a guide (21, 31) extending in a direction from the proximal end to the distal end, a sliding element (22, 32) comprising a shaft portion, extending inside the applicator body in a direction from the proximal end to the distal end and slidable along the guide of the applicator body and having a proximal end (22*a*, 32*a*) for handling by a user, the sliding element being provided at its distal end with a contact portion (22*b*, 32*b*) for contacting the spongeous collagen membrane (M), the contact portion being configured to extend to or past the distal end of the applicator body when sliding the sliding element, wherein the contact portion (22*b*, 32*b*) of the sliding element (22, 32) comprises mechanical fixation means (24, 34) configured to releasably hold the spongeous collagen membrane (M) without substantially generating forces acting in the distal direction on the spongeous collagen membrane over its area extension, wherein the distal end of the applicator body comprises a release surface (25, 35) configured to apply a release force to the spongeous collagen membrane (M) releasing it from the mechanical fixation means (24, 34) for application to a wound site (W), wherein the sliding element comprises a proximal portion (22*c*) extending proximally beyond the proximal end (20*a*) of the applicator body, and wherein the proximal portion of the sliding element protrudes out of the proximal end of the applicator body and a proximal end cap (20*b*), further comprising a biasing means (26, 36) biasing the sliding element (22, 32) and the applicator body (20, 30) with respect to each other along the direction of the guide (21. 31), wherein the biasing means (26, 36) biases the sliding element (22, 32) and the applicator body (20, 30) in a direction in which the contact portion (22*b*, 32*b*) of the sliding element is withdrawn proximally past the distal end of the applicator body, and wherein the contact portion (22*b*, 32*b*) is withdrawn into the applicator body and does not protrude beyond a distal opening (23, 33) of the distal end.

24. The applicator (2) according to claim 23, wherein the proximal end (20*a*) of the applicator body comprises the proximal end cap (20*b*) which engages the proximal end (20*a*) and is provided with a central opening through which the proximal portion (22*c*) of the sliding element (22) can pass.

25. The applicator of claim 23, wherein the proximal portion (22*c*) is a push-button.

* * * * *